United States Patent
Nose et al.

(10) Patent No.: US 9,433,409 B2
(45) Date of Patent: Sep. 6, 2016

(54) INSERTION NEEDLE

(75) Inventors: Kiyotaka Nose, Miyazaki (JP);
Kiyotaka Nagamine, Miyakonojo (JP);
Masateru Nagata, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 298 days.

(21) Appl. No.: 13/638,857

(22) PCT Filed: Apr. 1, 2011

(86) PCT No.: PCT/JP2011/058445
§ 371 (c)(1),
(2), (4) Date: Oct. 1, 2012

(87) PCT Pub. No.: WO2011/125947
PCT Pub. Date: Oct. 13, 2011

(65) Prior Publication Data
US 2013/0023725 A1    Jan. 24, 2013

(30) Foreign Application Priority Data

Apr. 1, 2010 (JP) ................................. 2010-085262

(51) Int. Cl.
*A61B 17/06* (2006.01)
*A61B 17/42* (2006.01)
*A61F 2/00* (2006.01)
(Continued)

(52) U.S. Cl.
CPC ......... *A61B 17/06109* (2013.01); *A61B 17/42* (2013.01); *A61B 17/0482* (2013.01); *A61B 17/06* (2013.01); *A61B 17/06066* (2013.01); *A61B 2017/00805* (2013.01); *A61B 2017/06019* (2013.01); *A61B 2017/06023* (2013.01); *A61B 2017/06042* (2013.01); *A61B 2017/06171* (2013.01); *A61F 2002/0072* (2013.01); *D05B 85/00* (2013.01); *D05B 85/06* (2013.01)

(58) Field of Classification Search
CPC .............. A61B 2017/0438; A61F 2220/0008;
D05B 85/00; D05B 85/006; D05B 85/02;
D05B 85/06; D05B 85/08; D05B 85/12;
D05B 85/14
USPC ............................................ 600/30; 606/144
See application file for complete search history.

(56) References Cited

U.S. PATENT DOCUMENTS 6,494,887 B1   12/2002   Kaladelfos
6,596,001 B2   7/2003    Stormby et al.
(Continued)

FOREIGN PATENT DOCUMENTS

JP   2003-038495   2/2003
JP   2003-512123   4/2003
(Continued)

*Primary Examiner* — Catherine B Kuhlman
*Assistant Examiner* — Shannon McBride
(74) *Attorney, Agent, or Firm* — Norris McLaughlin & Marcus, P.A.

(57) ABSTRACT

An insertion needle that is turnably mounted on a handle, which holds the insertion needle, wherein the insertion needle includes a turn arm that turns so as to face the tip of the insertion needle, and a target site that guides the insertion needle provided on the tip of the turn arm, and is further provided with: through-holes in two locations that are provided separated in the longitudinal direction of the tip of the insertion needle; an indentation formed between these through-holes; and a groove in the direction from the tip of the insertion needle toward the base of the insertion needle. Furthermore, the insertion needle is suitably used in urinary incontinence surgery, pelvic organ prolapse surgery or the like.

3 Claims, 11 Drawing Sheets

(51) Int. Cl.
*D05B 85/00* (2006.01)
*D05B 85/06* (2006.01)
*A61B 17/04* (2006.01)
*A61B 17/00* (2006.01)

(56) References Cited

U.S. PATENT DOCUMENTS 6,638,210 B2  10/2003  Berger
7,131,943 B2  11/2006  Kammerer
7,144,401 B2  12/2006  Yamamoto et al.
2011/0124954 A1*  5/2011  Ogdahl et al. ................ 600/30

FOREIGN PATENT DOCUMENTS

| JP | 2004-509685 | 4/2004 |
| JP | 2006-506104 | 2/2006 |
| JP | 2007-260385 | 10/2007 |

* cited by examiner

INSERTION NEEDLE

BACKGROUND OF THE INVENTION

The present invention relates to an insertion needle for insertion into a body cavity, such as for TVT (Tension-free Vaginal Tape) or TOT (Trans Obturator Tape) surgery that treats female urinary incontinence, and TVM (Tension-free Vaginal Mesh) surgery for pelvic organ prolapse.

The majority of female urinary incontinence is stress urinary incontinence. Females with stress urinary incontinence experience urinary incontinence during normal daily activities or movement, such as laughing, coughing, sneezing, or normal exercise.

Stress urinary incontinence is caused by a functional defect of the tissue or ligaments connecting to the urethra and pelvic bone; common factors for this include repetitive strain on the muscles in the pelvis, childbirth, loss of muscle tension in the pelvis, and a loss of female hormones. As a surgical treatment for stress urinary incontinence, TVT (Tension-free Vaginal Tape) surgery is common, and provides U-shaped reinforcement using tape made from polypropylene fiber, imagining the ligament passing through both sides of the pelvic bone and under the urethra, which is called the pelvic urethra ligament; in order to deliver the tape, a shaft, which has two comparatively thick, sharpened tips, must be used to pass through the vagina to reach the abdomen, and when inserting this shaft, the procedure is performed by way of groping, leading to a risk of damaging the structures inside the pelvis, such as the bladder, blood vessels, muscles, or nerves. Furthermore, to prevent this damage, visualization must be repeated by way of a cystoscope, and there is a disadvantage that a long time is required for surgery.

Various proposals have been made as countermeasures for this problem, but a fundamental means for solving the problem has yet to appear (see JP-2004-509685-A, for example).

Thus, in addition to the current TVT surgery described above, TOT (Trans Obturator Tape) surgery has been proposed as a new surgical method. This surgical method comprises the following steps.

(1) After performing anesthesia, a pair of right and left incisions is made in the skin at the obturator foramina and in the anterior vaginal wall. (A subcutaneous tunnel, of a size such as to allow a finger to be inserted, is created in the anterior vaginal wall.)

(2) A specialized insertion needle is inserted from the obturator foramen and comes out the anterior vaginal wall passing the back of the pubic bone. (At this time, a finger is inserted in the subcutaneous tunnel so as to guide the insertion needle.)

(3) After guiding the insertion needle from the anterior vaginal wall to outside the vagina, a tape is applied to a groove in the tip of the insertion needle, the insertion needle is extracted to outside of the skin, and the tape is drawn from the obturator foramen.

(4) The above operation is performed on the other obturator foramen side, and the tape is likewise drawn.

(5) After finely adjusting the tension of the tape drawn from the obturator foramina, the surgery is completed by suturing the skin and vagina.

Note that the above surgical method describes a method of pulling a needle from the obturator foramen to the vagina (outside in), but conversely a method of pulling from the vagina to the obturator foramen (inside out) is implemented with the same steps.

However, in the TOT surgery described above, a specialized insertion needle (for example a helical needle) is used and blindly inserted, and compared to conventional TVT, the distance the needle passes is short and is safe, but with an inexperienced surgeon, the insertion route cannot be reliably recognized, resulting in a risk of damaging the bladder, blood vessels, digestive tract or the like, causing serious complications.

Furthermore, pelvic organ prolapse is a separate disorder from which females suffer, which is similar to urinary incontinence. In this disorder, the pelvic organs, such as the uterus or bladder, which are being supported in a hammock shape by way of the pelvic floor muscle group, prolapse from the vagina due to weak pelvic floor muscles caused by aging or the like, which is so-called uterine prolapse or cystocele. Conventionally, as a repair method for pelvic organ prolapse, reinforcement colporrhaphy, wherein incisions were made in the vaginal wall and the prolapsed portion was shortened and stitched, was performed, but in recent years, as a substitute technique, TVM (Tension-free Vaginal Mesh) surgery for pelvic organ prolapse has been adopted, which make it possible to prevent the pelvic organs from prolapsing from the vagina by supporting the entire pelvic floor with polypropylene mesh in a hammock shape (see JP-2006-506104-A, for example).

SUMMARY OF THE INVENTION

However, the TVM surgery described above also requires a blind insertion procedure that uses a specialized insertion needle, similar to the TVT or TOT surgeries that treat urinary incontinence, and for an inexperienced surgeon, the insertion route cannot be reliably recognized, resulting in a risk of damaging the bladder, blood vessels, digestive tract or the like and of causing serious complications.

Moreover, there are problems in that it is difficult for non-surgeons to know where the inserted needle passes through, technical instructions are difficult, and a long time is required for learning the technique to reliable insert the needle. Furthermore, in the TVM surgery for pelvic organ prolapse, a procedure is required to pull out a thread, which is passed through a hole provided in the tip of the insertion needle, to outside the vagina by hooking with a hook, but for deep insertions, because the tip of the insertion needle is in a site deep inside the body, visibility is poor due to displacement of the surrounding internal organs, it is dark, and the location of the thread is different for each insertion procedure, thus there is a problem in that the hooking procedure with the hook is difficult and takes time.

In reflection of the problems described above, the present inventors, as a result of earnest research, provide an insertion needle that allows reliable insertion for TOT and TVT surgery for urinary incontinence and TVM surgery for pelvic organ prolapse.

Furthermore, an insertion needle that allows thread, which passes through the insertion needle, to be drawn in a short time, is provided.

Thus, a first characteristic of the insertion needle of the present invention is that of comprising through-holes in at least two locations that are provided separated in the longitudinal direction of the tip of the insertion needle and further comprising an indentation formed between these through-holes.

Furthermore, a second characteristic is that the insertion needle is provided with a groove from the tip of the insertion needle toward the base of said insertion needle.

Moreover, a third characteristic is that the insertion needle is provided with a hole, whereby the through-holes and the groove communicate.

Furthermore, a fourth characteristic is that an insertion needle is turnably mounted on a handle, which holds the insertion needle, wherein the insertion needle comprises a turn arm that turns opposite to the tip of the insertion needle, and a target site that guides the insertion needle that is provided on the tip of the turn arm.

Moreover, a fifth characteristic is that the insertion needle, which is turnably mounted on a handle, which holds the insertion needle, wherein the insertion needle comprises a turn arm that turns opposite to the tip of the insertion needle, and a target site that guides the insertion needle provided on the tip of the turn arm, is provided with a turning control means at a pivot of the turn arm.

Moreover, a sixth characteristic is that the insertion needle is used in urinary incontinence surgery.

Furthermore, a seventh characteristic is that the insertion needle is used in pelvic organ prolapse surgery.

By virtue of the insertion needle according to the present invention, because through-holes, which are made in at least two locations, which are provided separated in the longitudinal direction of the tip of the insertion needle, and an indentation, which is formed sandwiched between these through-holes, are further provided, an excellent effect is provided in that a thread, which passes through the through-holes, can be drawn reliably in a short time.

Moreover, because a groove from the tip of the insertion needle toward the handle that holds the insertion needle, and a hole, whereby the through-holes and the groove communicate, are further provided, excellent effects are provided in that an insertion procedure can be performed with the thread following along in the groove, so that there is no resistance by way of the thread being caught between the needle and body tissue during the surgery, and the procedure is easy to perform.

Furthermore, because the insertion needle is turnably mounted on the handle, which holds the insertion needle, and comprises a turn arm, which turns opposite to the insertion needle, and a target site, which guides the insertion needle that is provided on the tip of the turn arm, the insertion needle can be inserted always following a fixed course, thus excellent effects are provided whereby even an inexperienced surgeon can reliably perform insertion, so that no damage is done to the bladder, blood vessels, digestive tract or the like, and there is no risk of causing serious complications.

Moreover, because a turn control means is provided at the pivot of the turn arm, an excellent effect is provided wherein the body tissue is not injured by inserting the tip of the insertion needle to the target.

Furthermore, a desirable effect is provided wherein the insertion needle according to this invention is suitable for use in an insertion procedure with an insertion needle that is used in surgeries for urinary incontinence or for pelvic organ prolapse.

DETAILED DESCRIPTION OF THE INVENTION

Embodiment 1

Figure 1:
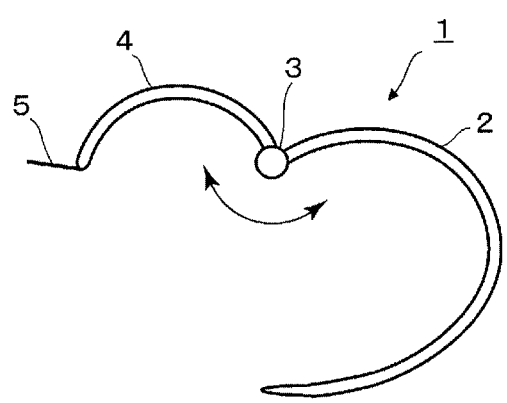
FIG. 1 is a schematic view showing an insertion needle according to the present invention.

As shown in FIG. 1, an insertion needle 1 of the present invention integrally comprises an insertion needle main body 2 that has a prescribed curved portion, an arm 4 that is attached via a pivot 3 provided on the base of the main body 2, and a target site 5 that is provided on the tip of the arm 4; and the insertion needle main body 2 and arm 4 turn with the pivot 3 as the center so that the tip of the insertion needle main body 2 is reliably guided to the target site 5.

Figure 2:
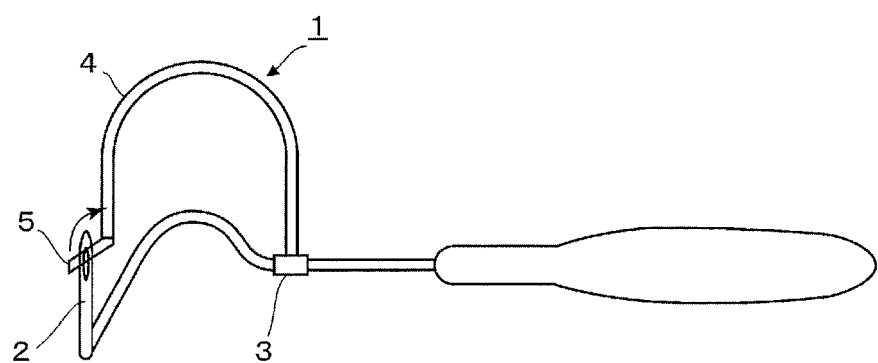
FIG. 2 is a schematic view showing another embodiment of the insertion needle according to the present invention.

FIG. 2 shows another embodiment of the insertion needle of FIG. 1. The insertion needle 1 shown in the drawing is such that the insertion needle main body 2 has a curved shape, and the far-sighted needle main body 2 turns so as to contact or be inserted into the target site 5, which is provided on the tip of the arm 4 that is attached via the pivot 3.

Figure 3A:
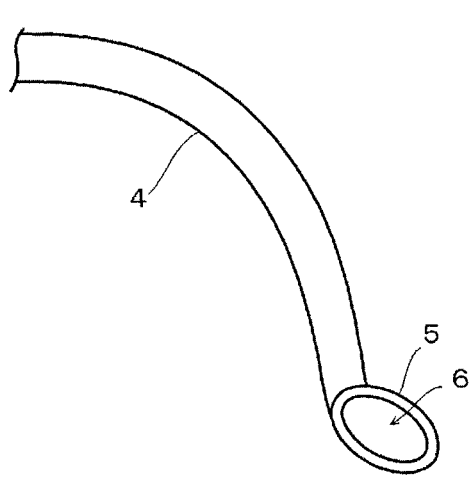
FIGS. 3(a) and 3(b) are schematic views showing the shape of a target site.
Figure 3B:
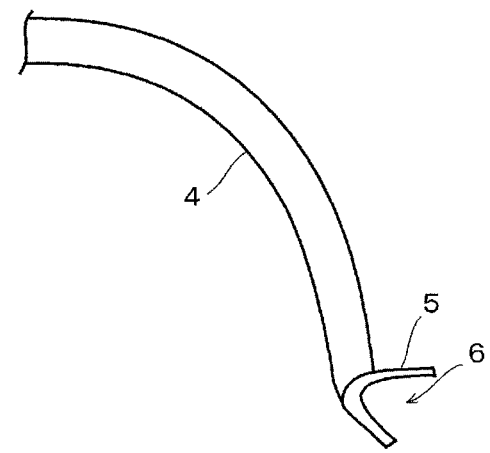

FIGS. 3(a) and 3(b) show the shape of the target site 5; FIG. 3 (a) shows a ring type, and FIG. 3 (b) shows a V-shape type. As shown in the drawing, a target center site 6 is formed in the approximate center of the target site 5, and the tip of the aforementioned insertion needle main body 2 is guided to the target center site 6.

Figure 4B:
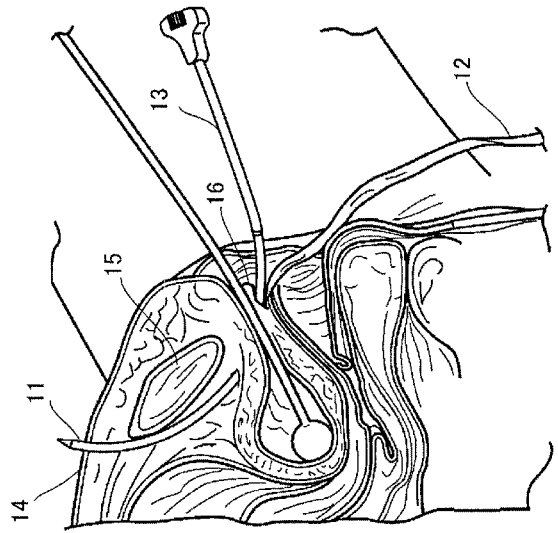
FIGS. 4(a) and 4(b) are schematic views showing a conventional TVT surgery.
Figure 4A:
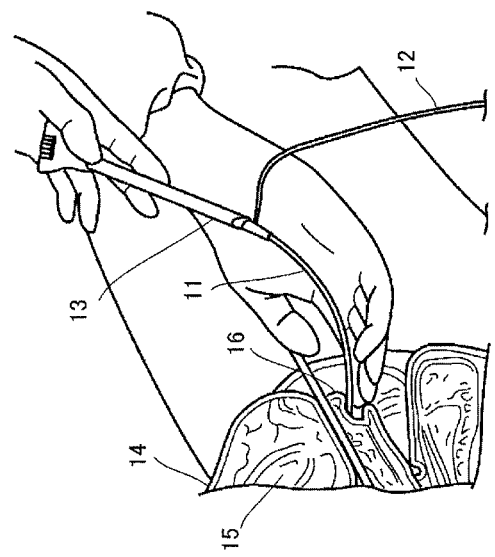
Figure 5B:
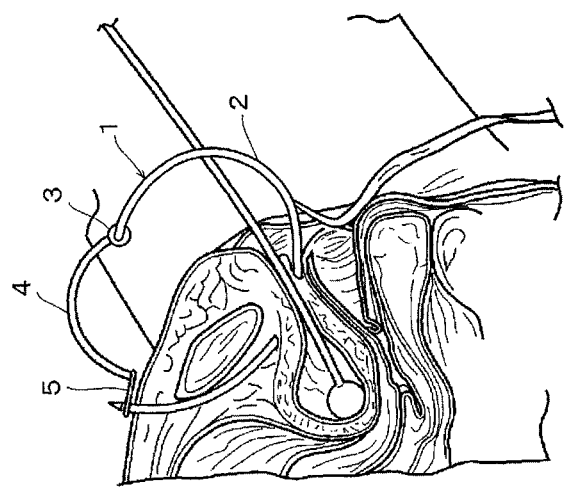
FIGS. 5(a) and 5(b) are schematic views showing a TVT surgery using the insertion needle of the present invention.
Figure 5A:
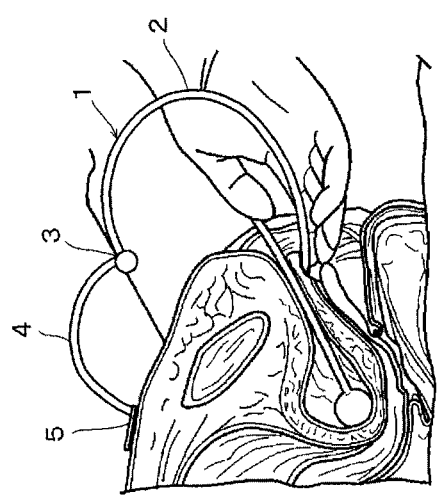

An example of use for the insertion needle 1 with the above configuration is described in detail in accordance with drawings that describe a urinary incontinence surgery (TVT surgery). FIGS. 4(a) and 4(b) are schematic views showing a conventional TVT surgery; FIG. 4 (a) is a schematic view showing the situation before insertion, and FIG. 4 (b) is a schematic view showing the inserted state. FIGS. 5(a) and 5(b) are schematic views showing a TVT surgery using the insertion needle 1 of the present invention; FIG. 5 (a) is a schematic view showing before insertion, and FIG. 5 (b) is a schematic view showing the inserted state.

As shown in FIGS. 4(a) and 4(b), for the conventional TVT surgery, incisions are opened in advance in the abdominal skin 14 (on the left and right above the pubic bone 15) and the anterior vaginal wall 16 of the patient; a subcutaneous tunnel, of a size such as to allow a finger to be inserted, is created in the anterior vaginal wall 16; and an insertion needle 11 mounted on a specialized handle 13 is placed in the subcutaneous tunnel location. Then, the insertion needle 11 is blindly inserted so as to pass a mesh tape 12 through to a first incision location in the abdominal skin 14. In the same manner, the insertion needle 11 passes the mesh tape 12 through to a second incision location in the abdominal skin 14; the mesh tape 12, which has been pulled out from the abdominal skin 14 to the right and left, is positioned by fine adjustments; and the surgery is completed by suturing the incisions in the abdominal skin 14 and anterior vaginal wall 16. With the TVT surgery according to the conventional method, because the insertion needle 11 is blindly inserted from the subcutaneous tunnel in the anterior vaginal wall 18 to the abdominal skin 14 location, there is a risk of complications, such as injury to the bladder or vascular injury.

In contrast, in the TVT surgery that uses the insertion needle 1 of the present invention shown in FIGS. 5(a) and 5(b), the insertion needle main body 2 is put in the location of the subcutaneous tunnel, in the same manner as with the conventional TVT surgery above. Next, the target site 5, which is provided on the tip of the arm 4, is placed on the location of an incision in the abdominal skin. Then, when the arm 4 and insertion needle main body 2 are turned united with the pivot 3 as the center, and insertion is made from the subcutaneous tunnel location, the tip site of the insertion needle main body 2 reliably reaches the target site 5 location. Thus, the surgeon who is performing the surgery can reliably insert, without blindly inserting, the insertion needle 1. Furthermore, because even an inexperienced surgeon can reliably perform insertion, the risk of complications, such as injury to the bladder or vascular injury, is very low. Note that the surgical procedures after insertions are the same as the above conventional surgery, and therefore have been omitted.

The insertion needle of the present invention with the above configuration can be suitably used for urinary incontinence surgery (TVT surgery), and can also be used in the same manner for the aforementioned TOT surgery; the insertion needle and arm can be modified in various modes.

Embodiment 2

Figure 6B:
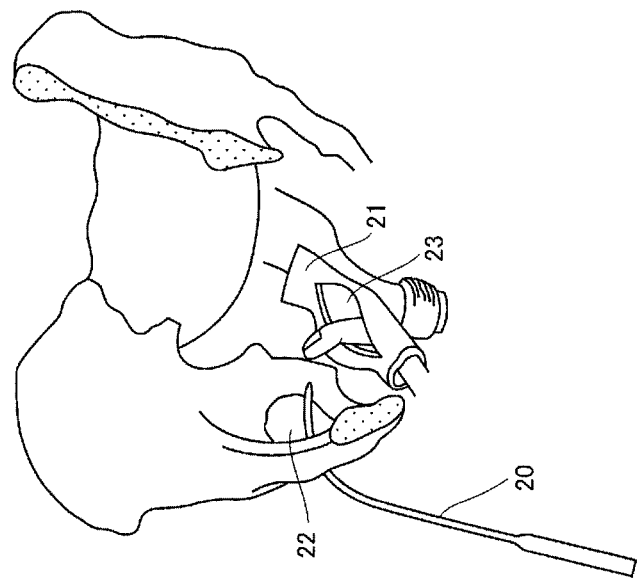
FIGS. 6(a) and 6(b) are schematic views showing a conventional TVM surgery.
Figure 6A:
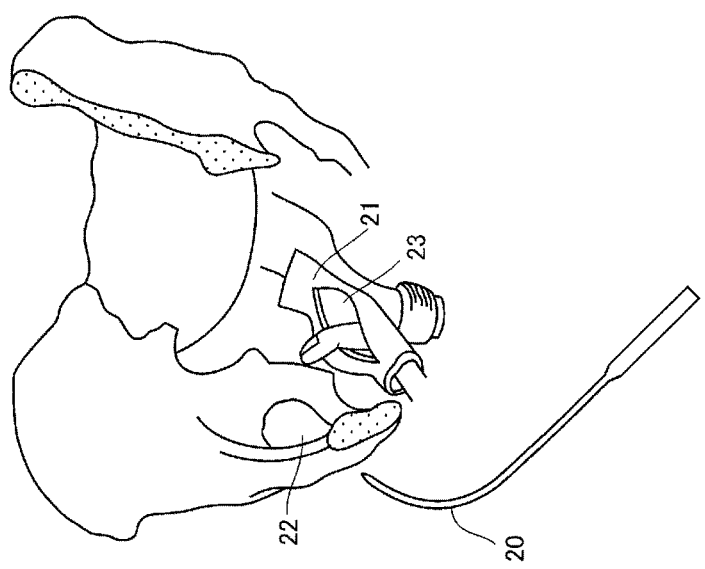
Figure 9:
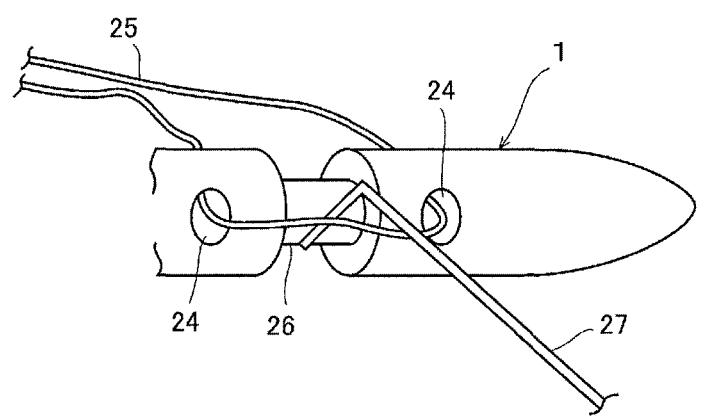
FIG. 9 is a partial enlarged view of the tip of the insertion needle of the present invention.

Next, pelvic organ prolapse surgery (TVM surgery) using the insertion needle of this invention is described in accordance with FIGS. 6(a) to 6(b) to FIG. 9. TVM surgery supports pelvic organs, such as the uterus or bladder, with a polypropylene mesh in a hammock shape such that the prolapse of pelvic organs from the vagina is prevented, and reinforces the vaginal anterior or the vaginal posterior with the mesh, by way of known surgical methods indicated in the abovementioned JP-2006-506104-A or the like.

Figure 7A:
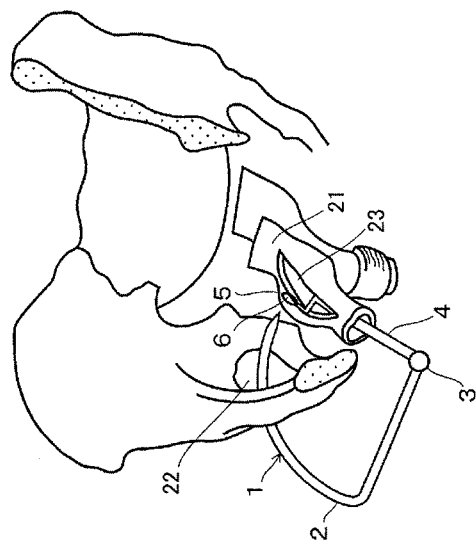
FIGS. 7(a) and 7(b) are schematic views showing a TVM surgery using the insertion needle of the present invention.
Figure 7B:
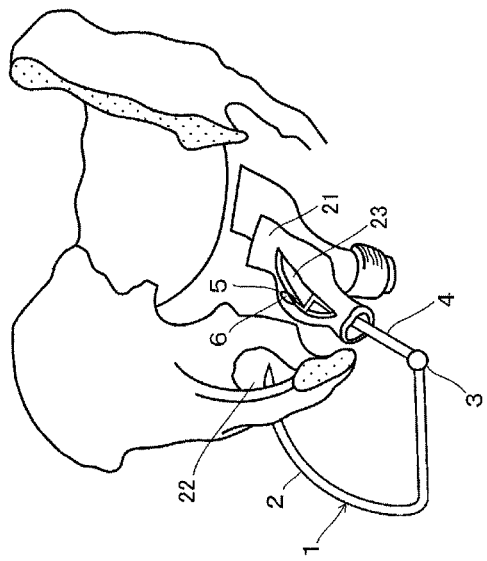

FIGS. 6(a) and 6(b) show the insertion state during reinforcement of the anterior vaginal wall by way of conventional TVM surgery; FIG. 6(a) shows the situation where an insertion needle 20 is inserted through the obturator foramen; and FIG. 6(b) shows the situation where the tip of the insertion needle 20 is blindly guided to the finger of the surgeon. Furthermore. FIGS. 7(a) and 7(b) show the insertion state during reinforcement of the anterior vaginal wall by way of TVM surgery, using the insertion needle of the present invention; FIG. 7(a) shows the situation where the arm 4 is inserted in the colpotomy and the insertion needle main body 2 is inserted through the obturator foramen; and FIG. 7(b) shows the situation where the insertion needle 1 is turned united with the insertion needle main body 2 so that the tip thereof is guided to the target site 5.

Hereafter, the surgery to reinforce the anterior vaginal wall by way of TVM surgery using the insertion needle of the present invention is described in accordance with the drawings; first, the anterior vaginal wall 21 is cut with scissors, a space is sufficiently opened so that the mesh (not shown) can be inserted, and incisions are made at two locations each at the right and left obturator foramen 22.

Then, the tip of the insertion needle main body 2 is placed in the position of the incision at the obturator foramen 22, and, with the finger of the surgeon in contact, the target site 5 on the arm 4 is inserted so as to be disposed in the incision 23 location of the anterior vaginal wall 21. Then, the insertion needle main body 2 and arm 4 are turned united with the pivot 3 as the center, and the insertion needle main body 2 is inserted from the obturator foramen 22, so that the tip of the insertion needle main body 2 reliably reaches the location of the target center site 6 of the target site 5. After the insertion procedure, a procedure to pull out a string of the mesh is performed, and the mesh is disposed in a suitable location on the anterior vaginal wall 21.

As described above, if the TVM surgery is performed using the insertion needle 1 of the present invention, then even an inexperienced surgeon can reliably recognize the insertion route, and no damage is done to the bladder, blood vessels, intestinal tract or the like, and the risk of accompanying serious complications is low. Moreover, because even those who are not surgeons can easily understand where the insertion needle, which is inserted, passes through, the technical instruction is also simple, and the technique for reliably inserting the insertion needle can be learned in a short time.

Figure 8:
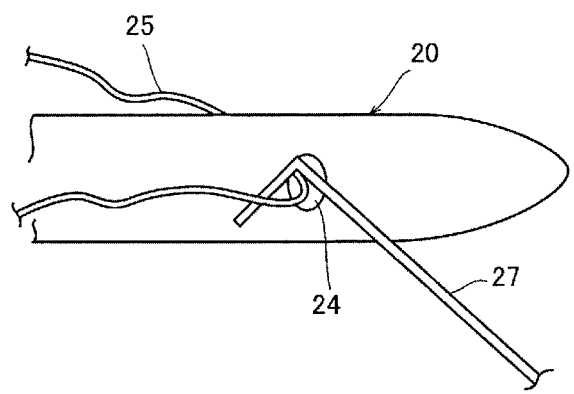
FIG. 8 is a partial enlarged view of the tip of a conventional insertion needle.

FIG. 8 and FIG. 9 show the tip of the insertion needle; FIG. 8 shows the tip of a conventional insertion needle, and FIG. 9 shows the tip of the insertion needle of the present invention. As shown in the drawings, the conventional insertion needle 20, which has a single through-hole 24, which is for passing a thread, is made adjacent to the tip thereof, and is used by inserting a thread 25 for drawing the mesh or the like. Furthermore, in the tip of the insertion needle 1 of the present invention, two through-holes 24, 24 for passing a thread, are provided separated in the longitudinal direction, and an indentation 26 is provided, sandwiched between these through-holes 24.

In performing the pelvic organ prolapse surgery (TVM surgery) described above, using the insertion needles 1 and 20 with the above configurations, there are, in both cases, procedures for pulling out a thread 25, which serves to draw the mesh, by way of a hook 27, and both require searching by way of groping for the tip of the insertion needle 1 or 20, which is inserted into a site deep inside the body. Thus, with the conventional insertion needle 20, the pulling procedure took a long time because the location of the thread 25 was not fixed. In contrast, with the insertion needle 1 of the present invention, because the thread 25 is used in a state of being inserted in two through-holes 24, the thread 25 can be reliably pulled simply by guiding the hook 27 to the location of the aforementioned indentation 26.

Embodiment 3

Figures 10A, 10B, 10C:
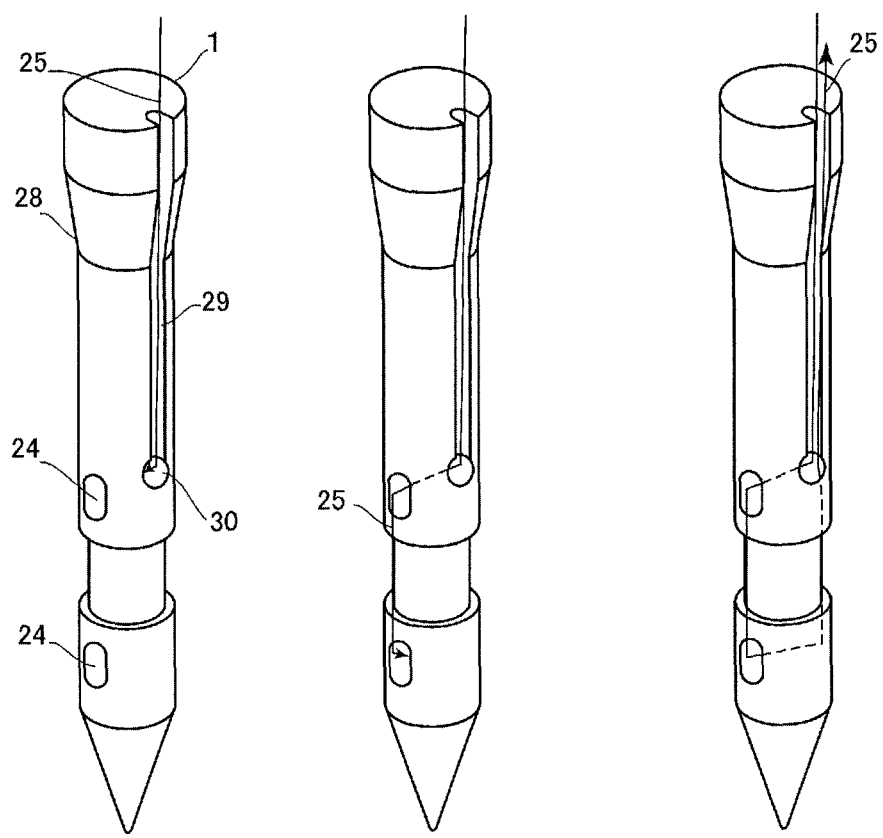
FIGS. 10(a), 10(b) and 10(c) are partial enlarged views of the tip structure of the insertion needle of the present invention.

FIGS. 10(a), 10(b) and 10(c) show another embodiment of the insertion needle of FIG. 9; FIGS. 10(a) to 10(c) show the process for passing the thread 25 through. As shown in the drawing, a groove 29 is provided longitudinally at a prescribed depth on a base 28 of the insertion needle 1. Moreover, a hole 30 is made in a prescribed location on the groove 29, the thread 25 can be passed through between the hole 30 and the through-hole 24 that is closer to the base end. With a view to passing the thread 25 through the insertion needle 1, the thread 25 is passed through to the hole 30 from the base end along the groove 29, and then is further pulled from one side of the through-hole 24 that is closer to the base end. Next, the thread 25 is inserted into the through-hole 24 on the tip end and is extended to the base end of the insertion needle 1, then this is pulled from the hole 30 after being inserted through the other side of the through-hole 24 that is closer to the tip end, and is pulled along the groove 29 to the base end of the insertion needle 1.

When using the thread 25, which passes through the insertion needle 1 with the above configuration, in the pelvic organ prolapse surgery (TVM surgery) described above, insertion is possible with both ends of the thread 25 drawn to the base end of the insertion needle 1 along the groove 29 of the insertion needle 1, and during the insertion procedure, the thread 25 lies between the insertion needle 1 and body issue, and does not resist when the thread 25 is drawn by way of the hook 27, so that the procedure can be safely done. Note that although the description of this embodiment of the insertion needle is for the case where the hole 30 and the groove 29 are provided, the groove 29 alone may be provided, and either insertion needle will have the same effect.

Embodiment 4

Figure 11:
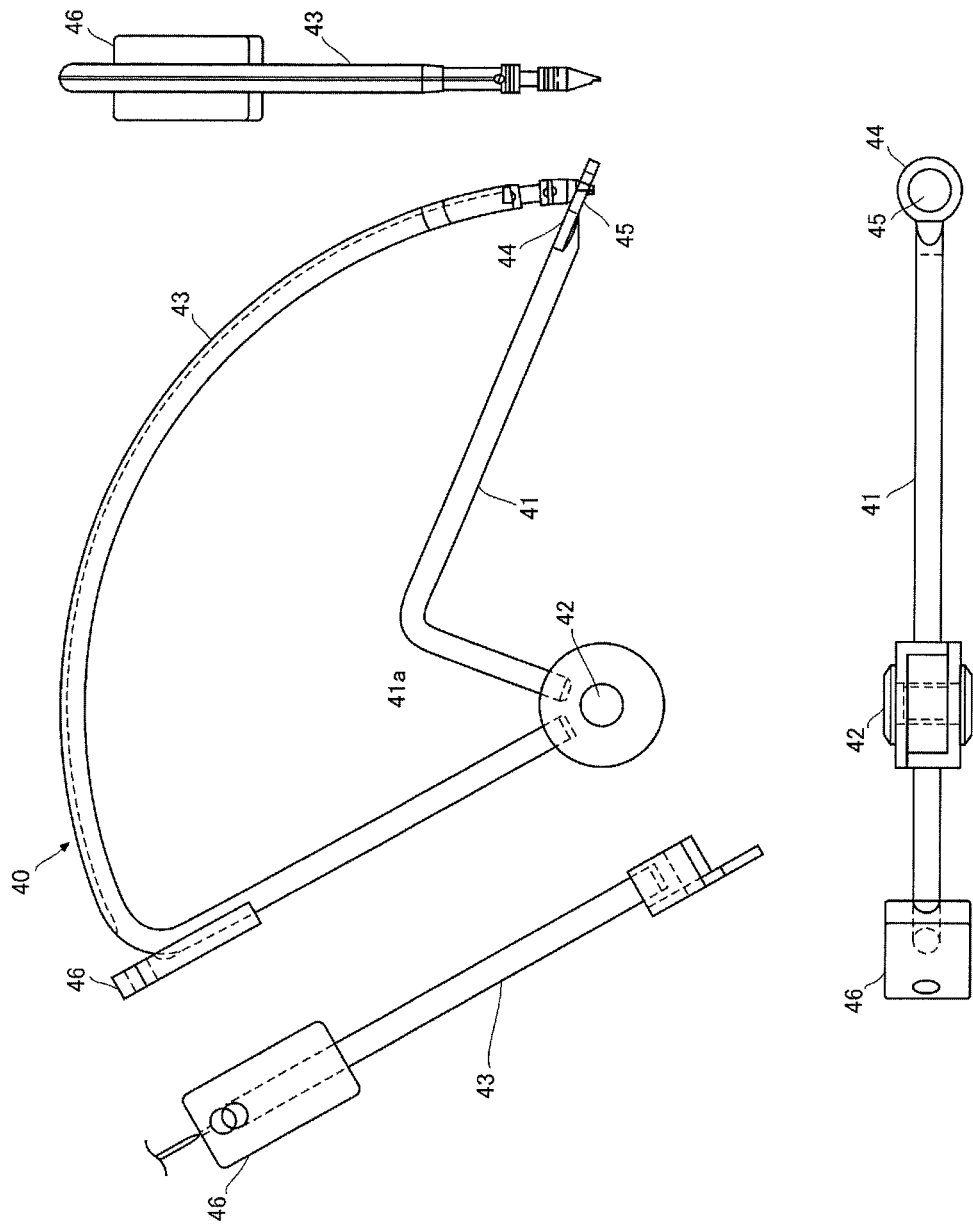
FIG. 11 is a schematic view of the overall structure of the insertion needle of the present invention.

FIG. 11 shows another embodiment of the insertion needle having a grooved configuration of FIGS. 10(a), 10(b) and 10(c). As shown in the drawing, a insertion needle 40 comprises an L-shaped arm 41; a pivot 42, and a insertion needle main body 43; the insertion needle main body 43 rotates around the pivot 42; and the tip of the insertion needle main body is inserted in a target center site 45 of the target site 44 that is provided on the tip of the arm 41. A stopper (not shown in the drawing) is provided in the pivot 42, so that the rotation is restricted to positions where no damage is caused to body tissue when the insertion needle main body 43 is inserted into the target site center site 45. Furthermore, either 20 mm or 40 mm is used for the length of a pivot-end arm 41a of the L-shaped arm 41, this being suitably selected according to the insertion procedure method (anterior insertion or posterior insertion). Moreover, in a prescribed location on the insertion needle main body 43 toward the pivot 42 end, a plate 46, which is wider than the diameter of the insertion needle main body 43, is mounted, which is structured for easy pushing, such that a hand (finger) can be placed there during the insertion procedure.

Note that the target site 44 in the drawing is described with a round through type, but may also be other shapes (for example a Y-shape), and may also be such that the target center site 45 does not pass therethrough.

As described above, by virtue of the insertion needle of the present invention, the insertion needle can be reliably inserted in any of the methods described above. That is to say, even an inexperienced surgeon can reliably recognize the insertion route so as to insert the insertion needle, no damage is done to the bladder, blood vessels, intestinal tract or the like, and the risk of accompanying serious complications is low. Moreover, even those who are not surgeons can easily recognize the insertion needle location; TVT and TOT surgery for urinary incontinence and TVM surgery for pelvic organ prolapse can be safely performed; and the technical instructions and technical learning for these surgeries is simple. Furthermore, the insertion needle of the present invention allows for obvious applications in other surgeries or techniques that require procedures of inserting a needle by way of the methods described above so as to pass a thread, catheter, mesh or the like.

The invention claimed is:

1. A surgical needle apparatus, comprising:
a main body configured as a needle so as to have a distal end adapted to insert into a body cavity or through tissue, and having a proximal end opposite the distal end;
the main body extending so as to curve along a length from the proximal end to the distal end;
the main body having a radially-extending first passage in a first plane transverse to said length at a first longitudinal location along said length, and having a radially-extending second passage at a second plane transverse to said length at a second longitudinal location along said length;
said first passage and said second passage each having a first opening adapted for passing a surgical thread therethrough;
the main body including a reduced-diameter first section along said length between said first longitudinal location and said second longitudinal location, said reduced-diameter section being solid along an entire length of said reduced-diameter section and adapted so that said surgical thread would traverse exterior to an outer surface of said reduced-diameter section as the surgical thread extends from the first passage to the second passage; and
the main body having a groove extending longitudinally along an outer surface of the main body from a second opening of said first passage toward said proximal end without traversing said reduced-diameter first section.

2. The surgical needle apparatus of claim 1, further comprising: a handle having said main body amiably mounted thereon; and
a turn arm that is turnable so as to face the distal end of the main body, and, on a tip of the turn arm, a guide for the surgical needle apparatus.

3. The surgical needle apparatus of claim 2, further comprising a pivot for the turn arm and a turning control at the pivot.

* * * * *